(12) United States Patent
Chimenti et al.

(10) Patent No.: US 7,160,728 B2
(45) Date of Patent: Jan. 9, 2007

(54) METHODS FOR OPTIMAL USAGE AND IMPROVED VALUATION OF CORROSIVE PETROLEUM FEEDSTOCKS AND FRACTIONS (LAW521)

(75) Inventors: Robert J. L. Chimenti, Short Hills, NJ (US); Gerald M. Halpern, Bridgewater, NJ (US); Patricia H. Kalamaras, Milford, NJ (US); Michael P. Anderson, The Woodlands, TX (US); Maureen Iannucci, Sierra Madre, CA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 320 days.

(21) Appl. No.: 10/663,566

(22) Filed: Sep. 16, 2003

(65) Prior Publication Data

US 2004/0106204 A1    Jun. 3, 2004

Related U.S. Application Data

(63) Continuation of application No. 09/877,625, filed on Jun. 8, 2001, now abandoned, which is a continuation of application No. 09/274,744, filed on Mar. 23, 1999, now abandoned.

(51) Int. Cl.
 *G01N 33/24* (2006.01)
 *G01N 21/00* (2006.01)
(52) U.S. Cl. .......................... 436/29; 436/55; 436/164
(58) Field of Classification Search .................. 436/55, 436/29
See application file for complete search history.

(56) References Cited

U.S. PATENT DOCUMENTS 5,420,041 A * 5/1995 Matsushita et al. ........... 436/61
5,681,749 A * 10/1997 Ramamoorthy ............... 436/55

OTHER PUBLICATIONS

Dong et al. "Rapid determination of the carboxylic acid contribution to the total acid namber of lubricants by FTIR" http://www.thermal-lube.com/english/research/publications/mcgill_TANfinal.pdf, crated on-line Jul. 7, 2005.*
Robinson et al. "Monitoring oil degradation with infrared spectroscopy", http://www.wearcheck.ca/literature/techdoc/WZA018.pdf, created on-line Sep. 16, 2000.*
"Automated FTIR Method for Determination of the Base Number of Lubricants as an Alternative to ASTM D2896 . . . " http://www.priorartdatabase.com/IPCOM/000126654/.*
Van de Voort "FTIR Acid and Base Number Analyses: Their Potential to Replace ASTM Methods" http://www.thermal-lube.com/english/analytical/publications/TANTBNreplace.htm, 2001.*

* cited by examiner

*Primary Examiner*—Yelena G. Gakh
(74) *Attorney, Agent, or Firm*—Ronald D. Hantman

(57) ABSTRACT

The invention is a method to improve the prediction of the corrosivity of organic acids in petroleum crudes, feedstocks and distillation fractions by providing a more accurate, repeatable, and rapid means of determining the TAN from the IR spectrum of the material. The method can be easily practiced in refinery, terminal, and assay laboratories. It can be used in conjunction with models and hardware to optimize the usage and improve the valuation of corrosive feed stocks. The invention can be implemented on-line for blending optimization. It comprises the steps of irradiating a heated petroleum sample with IR radiation to produce its IR absorption spectrum, and predicting the TAN from the spectrum using a linear, multivariate regression model. The IR TAN value is then used as input to blending, valuation, and corrosion models.

24 Claims, 13 Drawing Sheets

Predicted IR TAN and Measured ASTM TAN for 221 Refinery Samples.

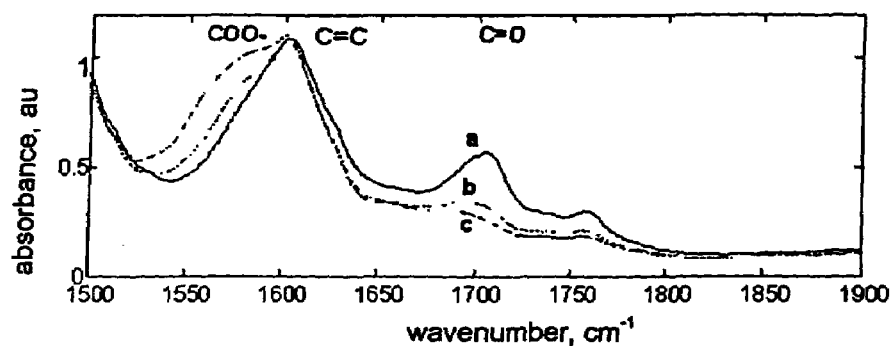
Fig. 1A. IR Absorbance Bands of C=O, Aromatic C=C, and Carboxylate COO- of a Distillate Residuum Fraction.

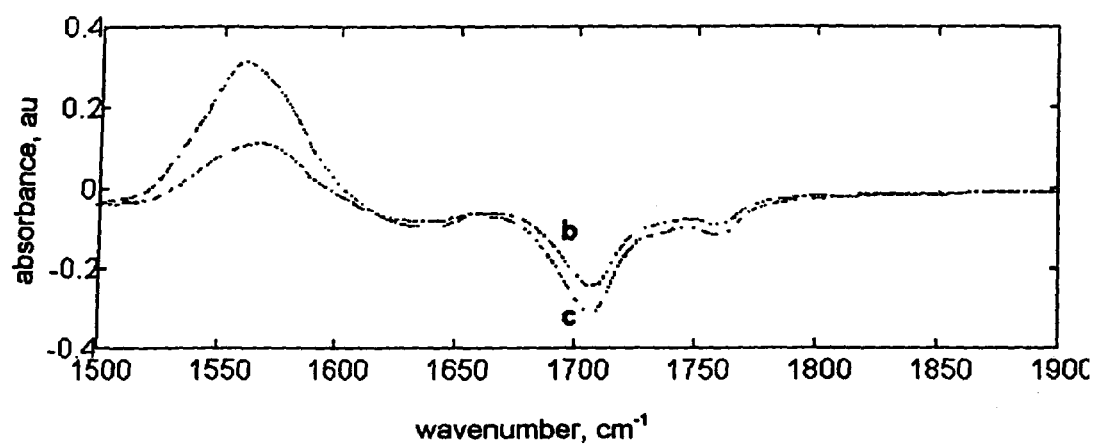
Fig. 1B. Absorbance Difference Between Treated Blends (curves b and c) and the Initially Untreated Blend of Distillate Residuum Fraction.

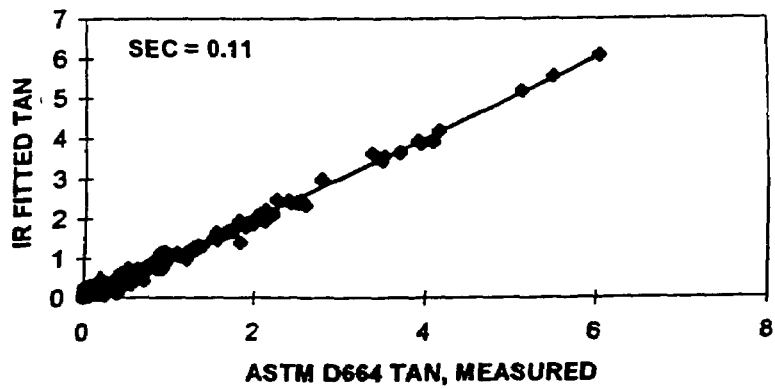
Fig. 2A. Fitted Values of IR TAN using the Calibration Model and Measured ASTM TAN for 216 Plant and Laboratory Distillation Samples.
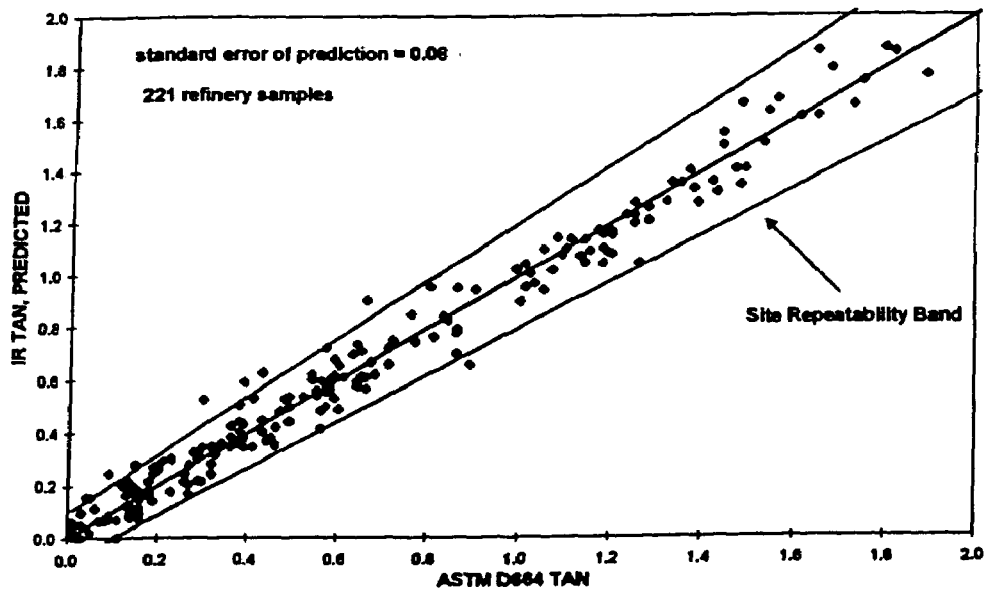
Fig. 2B. Predicted IR TAN and Measured ASTM TAN for 221 Refinery Samples.

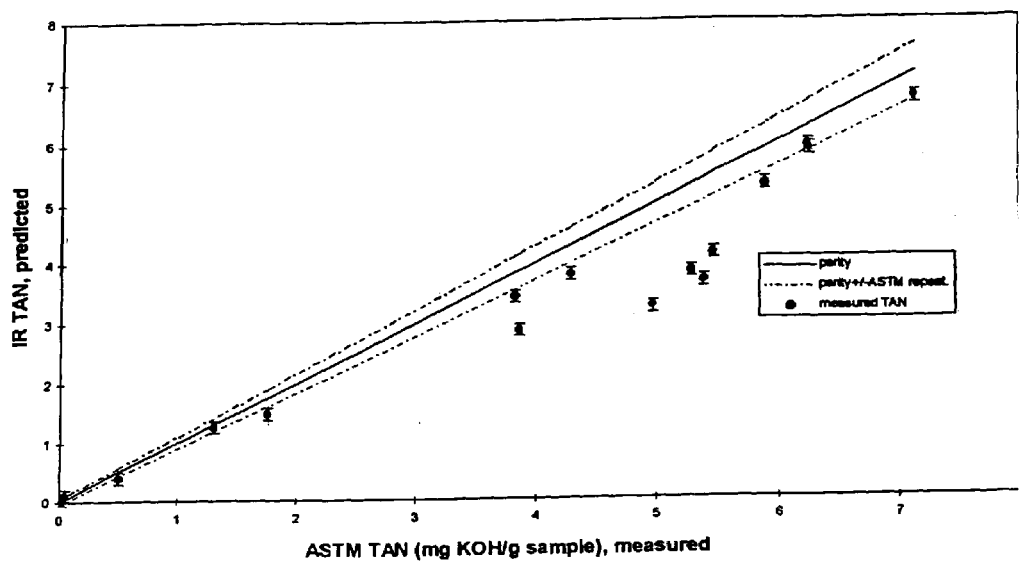
Fig. 3. IR TAN is Significantly Less than ASTM TAN for Samples with High Levels of Calcium Naphthanate.

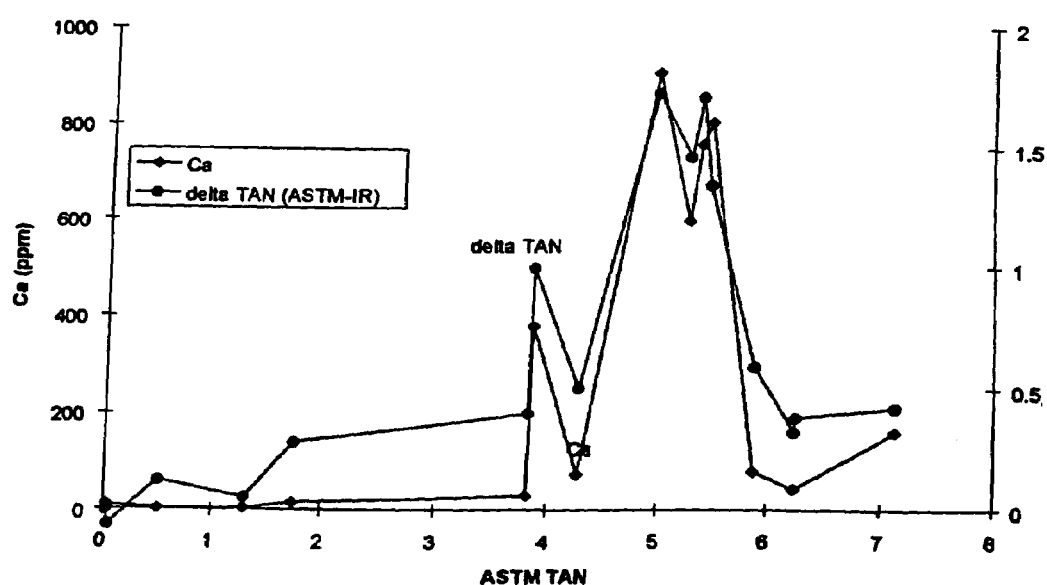
Fig. 4. Large Differences between IR and ASTM TAN Coincides with High Calcium Levels.

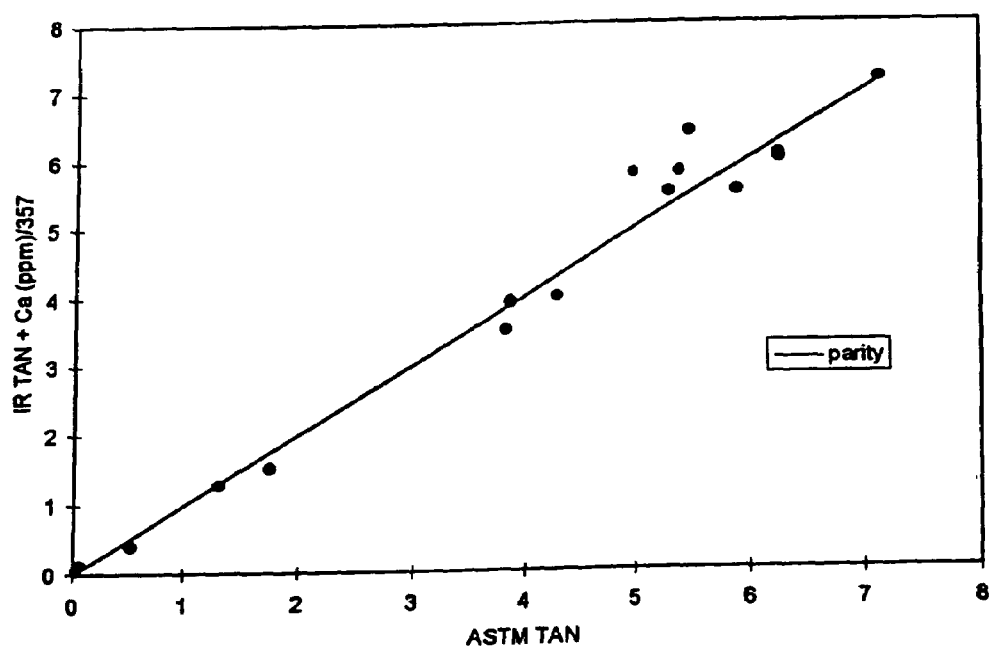
Fig. 5. Calcium Accounts for Difference between IR and ASTM TAN.

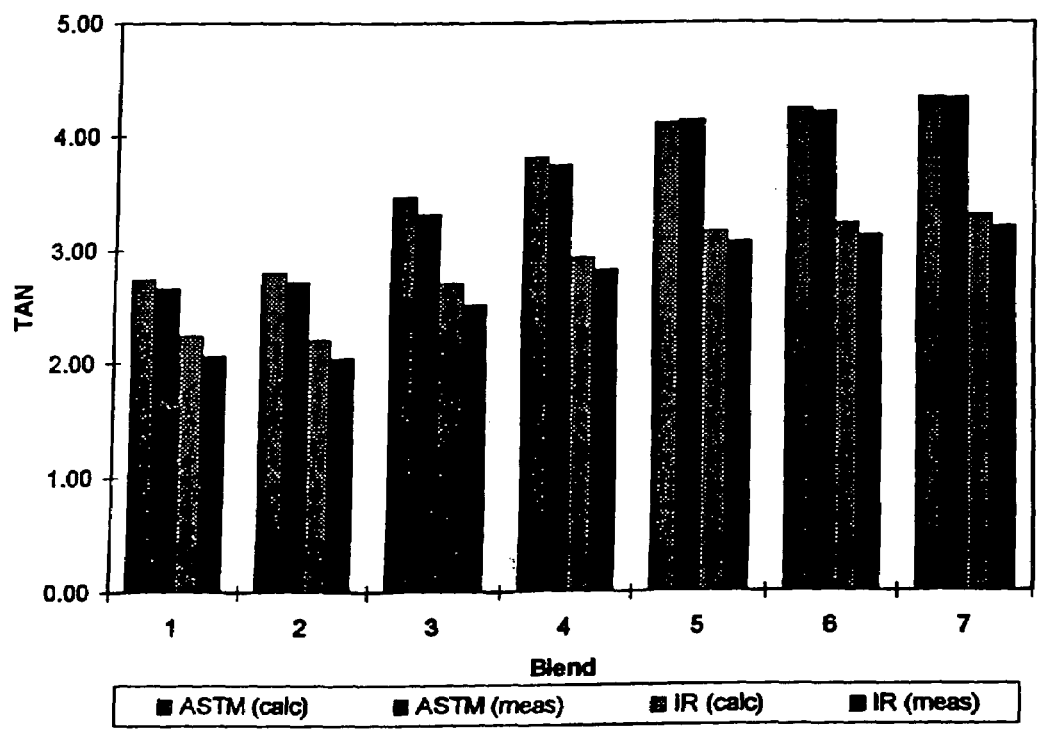
Fig. 6. IR TAN Blends Linearly and is Less than ASTM TAN for B, M, K Crude Blends.

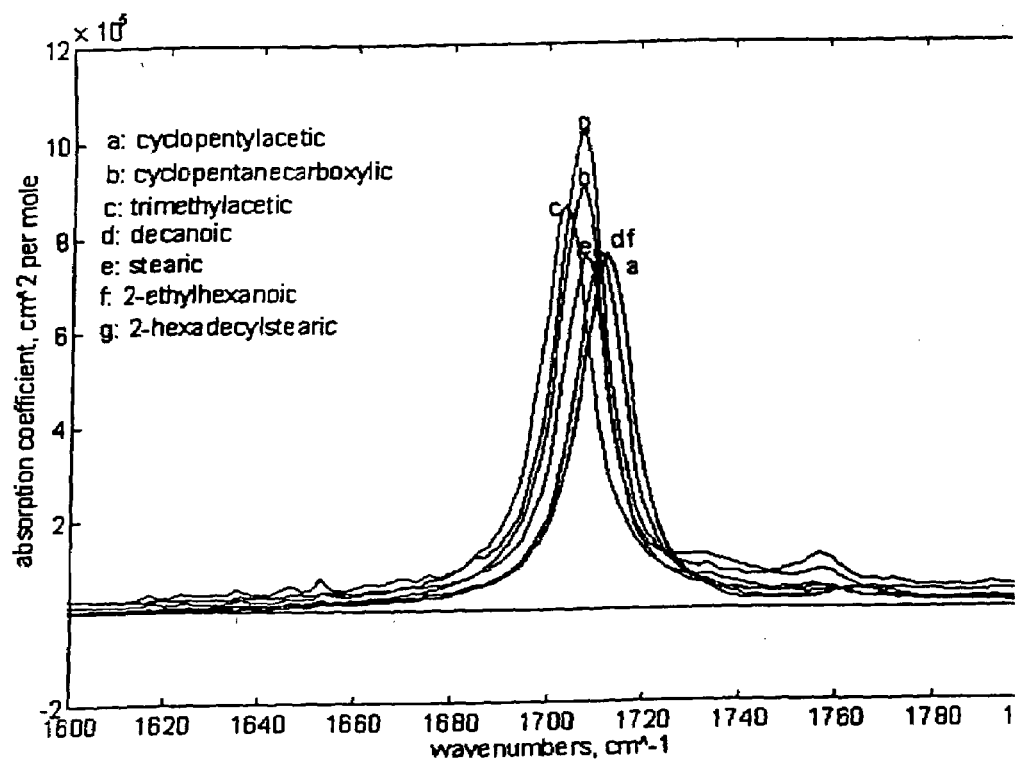
Fig. 7. Absorption Cross-Section of Model Acids Vary in Strength and Spectral Frequency.

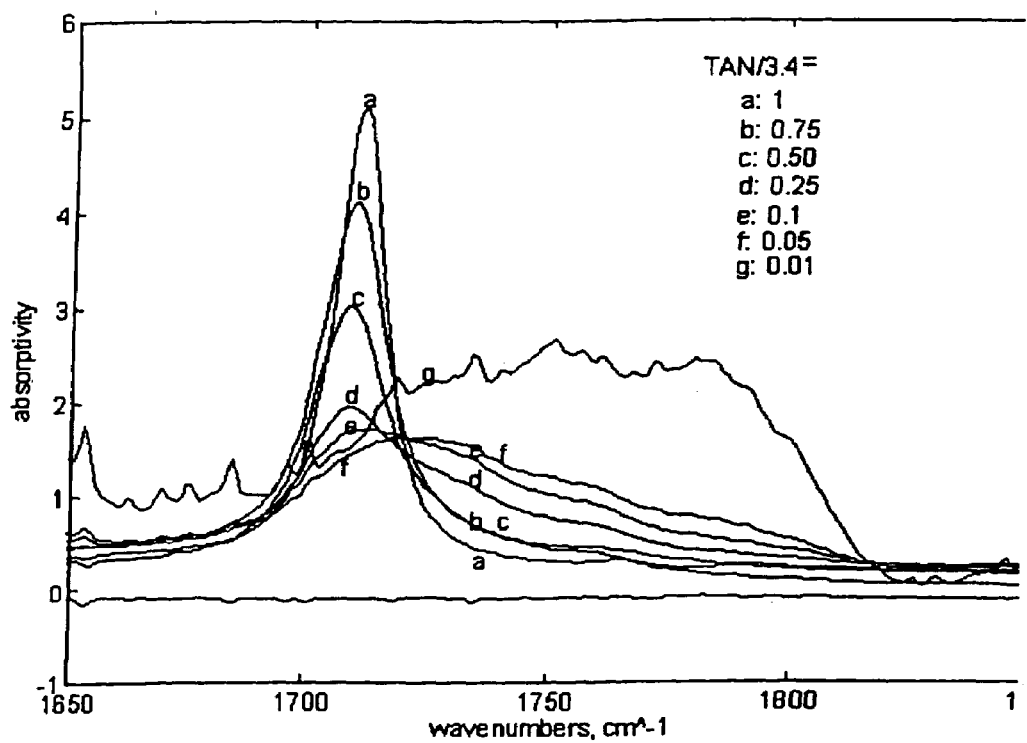
Fig. 8. Change in Shape of C=O Absorption Band with Concentration Due to Solvent Interactions.

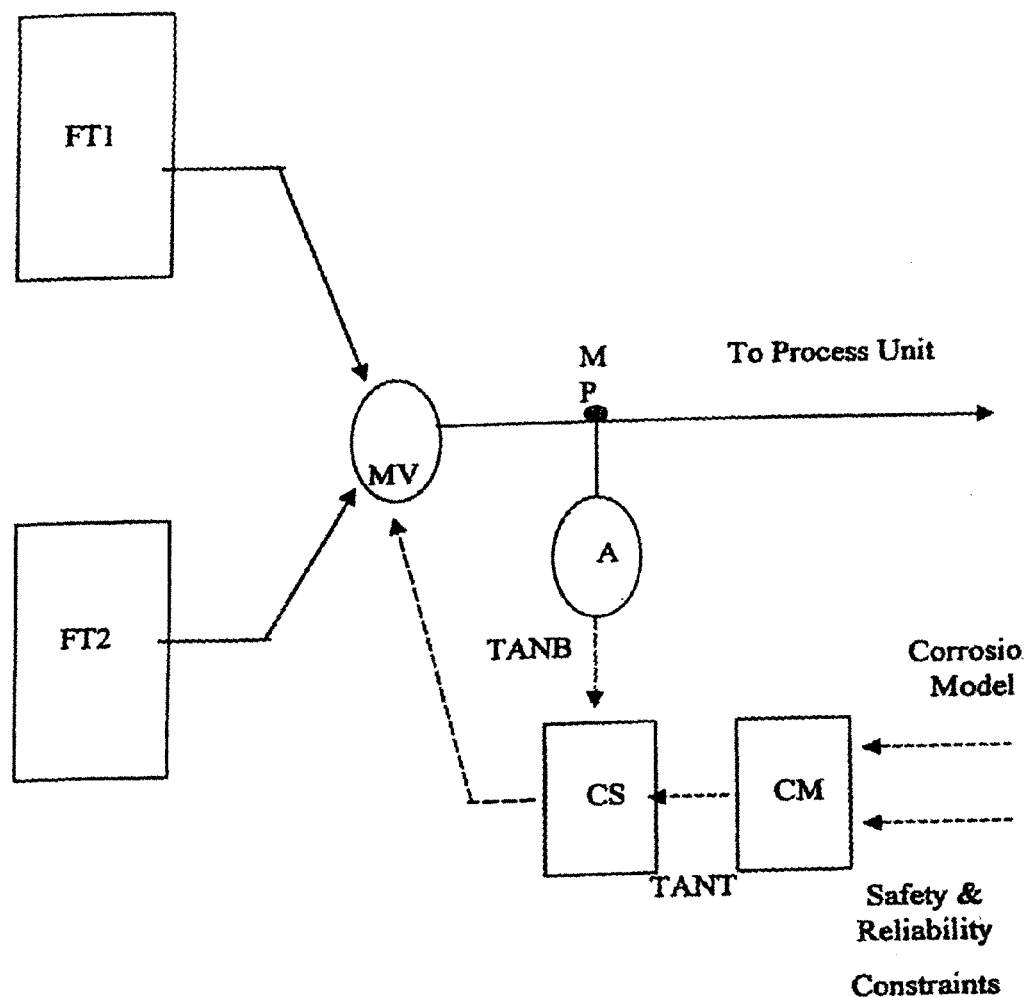
Fig. 9. Method to Optimize Blending High and Low TAN Feeds.

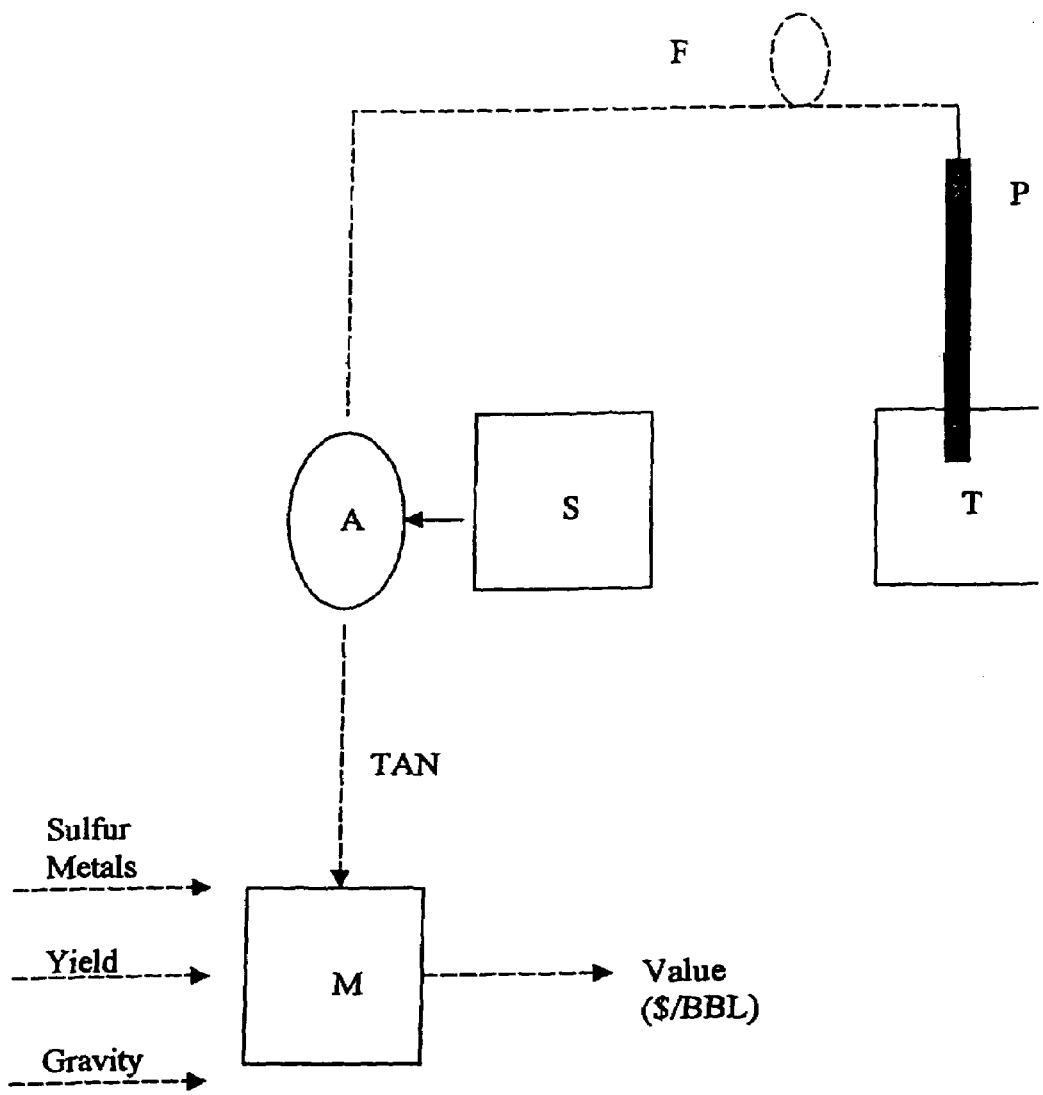
Fig. 10. Method to Optimize Valuation of Corrosive Crudes.

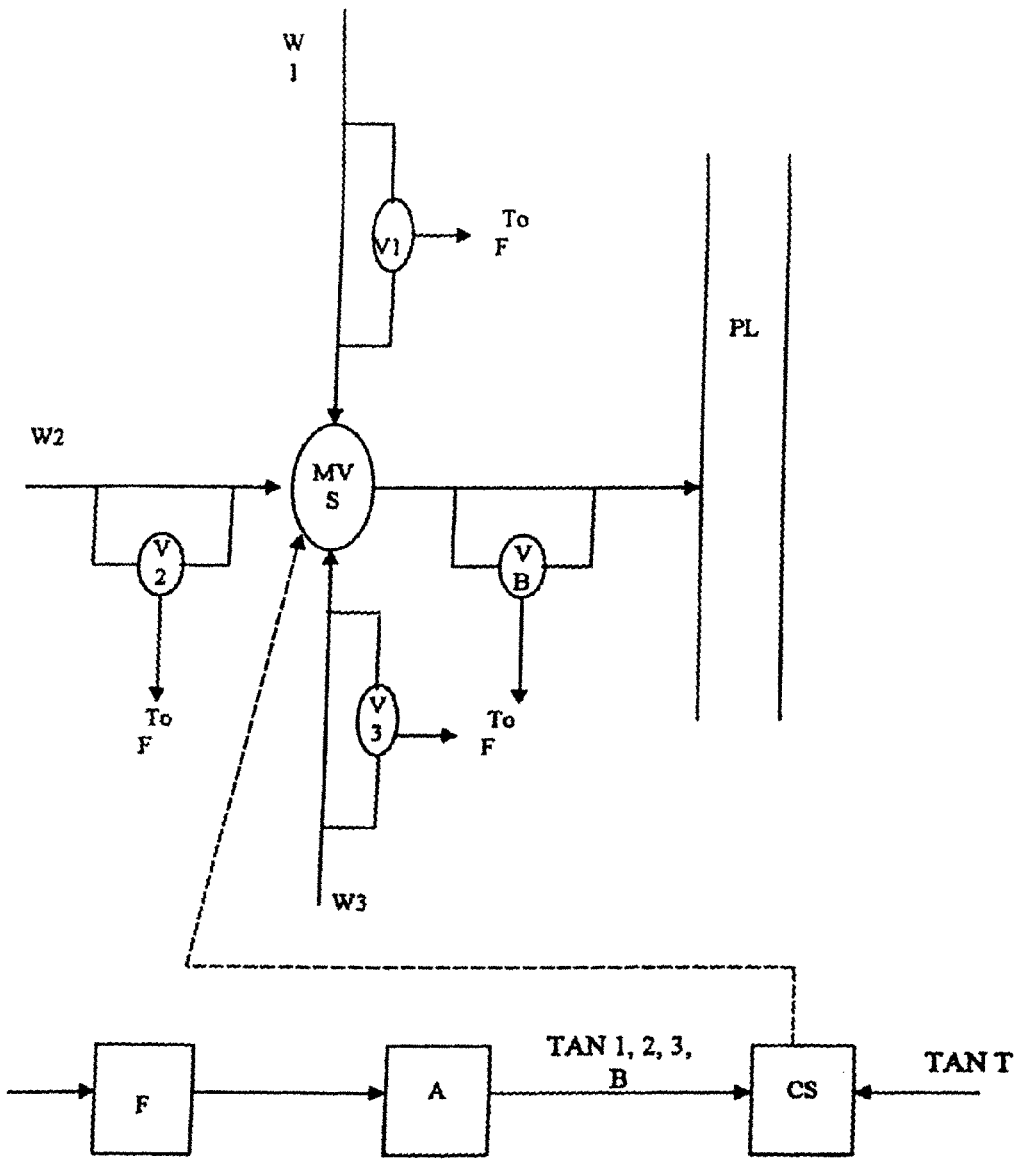
Fig. 11. Method to Optimize the Blending of Crude Oils from Different Wells a Target TAN for Pipeline Shipment.

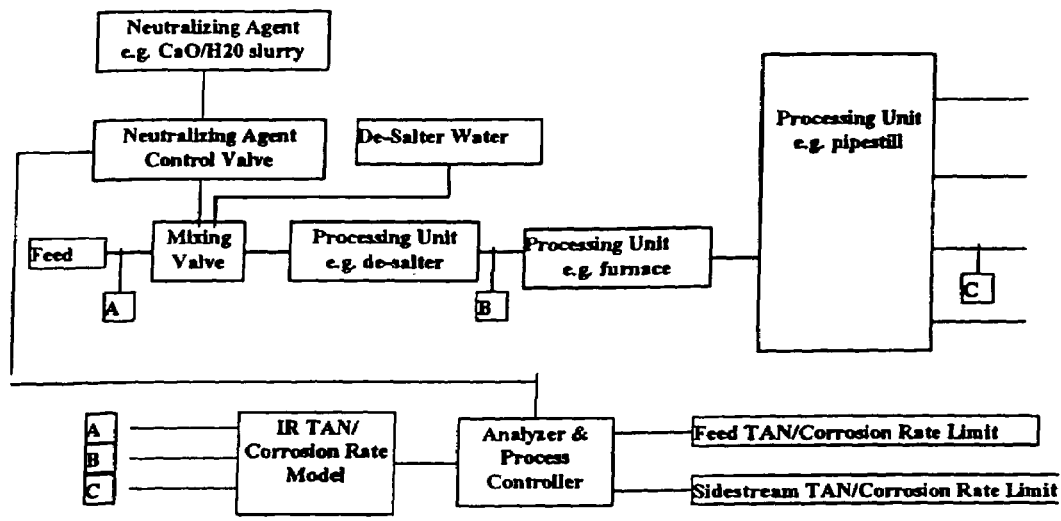
Fig. 12. Method to Optimize TAN Neutralization Process.

METHODS FOR OPTIMAL USAGE AND IMPROVED VALUATION OF CORROSIVE PETROLEUM FEEDSTOCKS AND FRACTIONS (LAW521)

CROSS-REFERENCE TO RELATED APPLICATION(S)

This application is a Continuation Under 37 C.F.R. § 1.53(b) of U.S. Ser. No. 09/877,625 filed Jun. 8, 2001 now abandoned which is a Continuation of U.S. Ser. No. 09/274,744 filed Mar. 23, 1999 now abandoned based on Patent Memorandum 96CL 074.

BACKGROUND OF THE INVENTION

This invention relates to a method for predicting the organic acid level in a petroleum feedstream and the use of that method. Substantial economic benefits derive from the optimal usage and improved valuation of corrosive feedstocks. Such benefits can be achieved by means of improved (i.e. more accurate, precise and rapid) methods for analyzing the corrosive organic acid content of these feedstocks which, in many cases, can be purchased at attractive prices. Additional benefits can be achieved through the use of these improved methods in conjunction with mathematical models to control process and blending apparatus and to valuate feedstocks. Applications of the means to obtain the improved organic acid content value, in conjunction with the models and control apparatus, are to predict the corrosivity towards process equipment, the value of a crude or blend for sale or purchase, the recipe for crude or feed blending to a target corrosivity or organic acid level and optimization of processes to reduce the corrosive organic acid species. The improved method for predicting the organic acid content is more accurate, repeatable, and rapid than existing methods and, unlike such existing methods, can be implemented for batch or continuous on-line operation.

Currently, producers, materials engineers, plant process operators and planners, and raw materials purchasers estimate corrosivity caused by the organic acids in the materials from the Total Acid Number (TAN), or a parameter derived therefrom, obtained by a commonly accepted potassium hydroxide titration method, one example being ASTM D664.

The ASTM D664 method, while the most commonly used method in the petroleum industry for determining organic acids in petroleum streams, is not selective to organic acids. It reports, as acids, any species that utilizes the potassium titrant in reaction, complexation, neutralization, or replacement. For example, one limitation of the current ASTM method is its inaccuracy in determining the correct acid content when the material has di- and trivalent metal acid salts, such as calcium naphthenates. Use of the ASTM TAN method on materials that contain calcium naphthenates would over-report the TAN since both true acid content as well as the calcium salts would be reported as TAN. Hence the corrosivity of the materials, as determined from mathematical models relating corrosion rates to the TAN value for these materials, would be over-estimated in such cases.

This invention includes, in all of its embodiments, a method to predict the organic acid content from the infra-red (IR) spectrum of a petroleum feedstock or process fluid. The IR method reports the organic acid content in units of titratable organic acid, TAN. The TAN determined by IR, henceforth called IR TAN, therefore, can be used in applications and models that use TAN as an input parameter. The IR TAN method is shown to be statistically equivalent to ASTM TAN and be more accurate than ASTM when calcium acid salts are present in the materials.

High TAN crudes can be purchased, in many cases, at attractive prices. The improved method for TAN measurement, as incorporated in the present invention, is a key enabler for reducing feed costs through the increased usage of such economically attractive materials.

SUMMARY OF THE INVENTION

The invention is a method to improve the prediction and control of the corrosivity of organic acids in petroleum crudes, feedstocks and distillation fractions by providing a more accurate, repeatable, and rapid means of determining the TAN from the IR spectrum of the material. The method can be easily practiced in field, refinery, terminal, and assay laboratories. It can be implemented on-line for blending optimization in production fields and in refineries.

The invention comprises the common steps of irradiating a heated petroleum sample with IR radiation to produce its IR absorption spectrum, and predicting the TAN from the spectrum using a multivariate regression model. The IR TAN value thus obtained is then used as input to blending, valuation, and corrosion models.

Other embodiments of the present invention include using the method of determining TAN level in methods for valuing crude oil, blending petroleum feed and distillation sidestreams and optimizing neutralizing processes.

BRIEF DESCRIPTION OF THE DRAWINGS

FIG. 1A shows the regions of the absorption bands of the acid C=O, aromatic C=C, and carboxylate ion COO— functionalities for the distillate residuum fraction of an untreated (curve a), and two treatment levels (curves b and c) of the crude oil blend of Example 1, where the treatment comprises the addition of Ca (OH)$_2$.

FIG. 1B shows the difference in absorbance of the untreated blend subtracted from each of the treated blends (curves b and c, respectively), of Example 1, showing the loss in acid C=O and gain in the salt COO— absorption.

FIG. 2A shows the fitted values of the IR TAN using the calibration model and corresponding measured ASTM TAN for 216 plant and laboratory distillation samples. Plant distillate fractions from atmospheric and vacuum pipestills and the material boiling at temperatures greater than 650° F. (650+) are included. Laboratory distillation fractions include a blend of material having mid-boiling point temperatures of 650 and 1050° F. and the total material that boils at temperatures greater than and less than 650° F., denoted by 650+ and 650−, respectively. The boiling point range for the lab cuts is 100° F. although some distillations were carried out with a 50° F. range for each cut. The Standard Error of Calibration (SEC) for all of the 216 samples is 0.11. The center solid line on the graph is the parity line.

FIG. 2B shows the predicted IR TAN and the measured ASTM TAN for 221 refinery samples using the calibration model shown in FIG. 2A. The Standard Error of Prediction is 0.08. It can be seen that the predictions are excellent with most of the data points around the parity line and within the site repeatability of the ASTM reference method.

FIG. 3 shows the IR and ASTM TAN values for high TAN crudes, some of which also contain high levels of calcium organic salts, as described in Example 2, below. Each data point is for a given sample measured by the two techniques with error bars representing the repeatability of the IR method. The solid line is the parity line and the band bounded by the dotted two lines surrounding the parity line represents values within the ASTM repeatability for the ASTM D664 method. Sample points lying outside and to the right of the region bounded by the two dotted lines in the figure are those for which the ASTM TAN is higher than the IR.

FIG. 4 shows that large difference between the ASTM and IR TAN coincides with high Ca levels in the samples. The triangle data points are the Ca levels in ppm, on the left ordinate axis, plotted against the ASTM TAN for the sample and sample sequence shown in FIG. 3. The circle data points are the delta TAN; that is, the difference between the ASTM and IR TAN measurements, right ordinate axis, for the same samples.

FIG. 5 shows the ASTM TAN, on the abscissa, for the same samples and sample sequence of FIG. 3 plotted against the sum of the IR TAN and the Ca-equivalent TAN (which is defined as the Ca (ppm)/357). The solid line is the parity line. The figure shows that the Ca in these samples can account for the differences between the measured IR and ASTM TAN.

FIG. 6 shows that for blends of high acid crudes having high levels of Ca naphthenates, the TAN values as measured and calculated, for both the ASTM and IR methods blend linearly. The IR TAN is lower in value for the blends consistent with the lower values for the blend components.

FIG. 7 shows that the absorption cross-section, in $cm^2$/mole, of model acids varies in peak position, spectral width, and dimer-to-monomer ratio. Thus, Beer's law, which expresses a linear relationship between concentration and spectral absorption, is not expected to hold for a complex mixture of acids present in a crude oil. Correspondingly, it is not obvious that a linear, multivariate model could be used to relate the spectra of this complex mixture to ASTM TAN with sufficient accuracy to be useful in the applications.

FIG. 8 shows that a single model organic acid dissolved in a white oil to a TAN value of 3.4 changes its spectral absorption band shape, not just intensity, as a function of concentration. Thus, Beer's law is not expected to hold for a complex mixture of acids present in a crude oil.

Correspondingly, it is not obvious that a linear, multivariate model could be used to relate the spectra of this complex mixture to ASTM TAN. It is, furthermore, not obvious that a single linear multivariate model for crudes and their distillate fractions could be developed having sufficient accuracy for corrosion applications, in view of the non-Beer's law behavior of the acids. For example, prediction error of 0.1 TAN units, over a sample set that includes crudes, pipestill and laboratory distillation cuts, is desirable.

FIG. 9 shows a method to optimize the blending of high and low TAN feeds to achieve a target TAN determined from a corrosion model and safety and equipment reliability constraints.

FIG. 10 shows a method to optimize the valuation of corrosive crudes by combining standard inspection qualities with the improved IR TAN method described herein.

FIG. 11 shows a method to optimize the blending of crudes from different wells to achieve a target TAN for shipment by pipeline or other transportation means.

FIG. 12 shows a method to optimize a TAN neutralization process.

DESCRIPTION OF PREFERRED EMBODIMENT

The novel features of this invention are its selectivity to organic acids, its ability to quantitate organic acid content in units of ASTM TAN, and its ability to predict acid content from IR spectra where the spectral frequency and band shape of the acid's absorbance changes with feedstock composition.

A method is described to predict the organic acid content, in ASTM D669 TAN units of mg KOH/gram of sample, of petroleum crude oils, laboratory and plant distillation fractions, and petroleum distillation residua. The method consists of the following:

1. For materials having boiling points below 1050° F., heating an undiluted sample to a temperature of 25 to 125° C., preferably between 40 and 100° C., and more preferably between 55 and 75° C. in an optical cell having a path length of 0.005 to 0.1 cm, preferably 0.01 to 0.03 cm, and more preferably 0.0175 to 0.0225 cm, so as to insure that the optical absorbance for every spectral frequency used in the model is between the values of 0 and 2.0 absorbance units, and preferably between 0 and 1.75 absorbance units, for every sample. The temperature is controlled to approximately ±2° C. for all measurements. Similarly the optical path length is fixed for all measurements.

2. For residua having boiling points above 1050° F., preparing and heating a mixture of known proportions of the crude or a distillation fraction boiling below 1050° F. (diluent fraction) and the fraction boiling above 1050° F. in the same optical cell as described above may be more convenient due to the high viscosity of the residuum fraction. Determination of the IR TAN for the residua is obtained by the difference between the IR TAN for the mixture and diluent fraction weighted according to their weight fractions. The use of a lower boiling fraction of the same crude as a diluent fraction avoids, to a greater extent, any mixture incompatibility, inhomogeneity, and precipitation that may occur if common reagent solvents are used.

3. Irradiate the heated sample with infra-red radiation in the spectral frequency ranges from 1000 to 4800 $cm^{-1}$ and preferably in the ranges 1000–1350 $cm^{-1}$, 1550–2200 $cm^{-1}$, 2400–2770 $cm^{-1}$, 3420–4800 $cm^{-1}$, and obtain the infra-red absorption spectrum of said sample.

4. Eliminate the major environmental and instrumental contributions to the measured spectrum by orthogonalizing the measured spectrum in each of the above mentioned frequency ranges to that of atmospheric air, dissolved water, and to orthonormal polynomials on each of the above mentioned frequency ranges representing the major instrumental contributions that are independent of the sample composition. The resulting spectra, called the conditioned spectra, are used as inputs in a multi-variate regression model.

5. Obtain the IR TAN value by multiplying the absorption at each spectral frequency used in the model by a calibration value for that frequency and summing up said products over all of the frequencies in the above-mentioned ranges.

6. The calibration values for each spectral frequency of the model are obtained by applying linear, multi-variate regression techniques to a data set consisting, in part, of the conditioned IR absorption spectra of samples for which the ASTM TAN had been obtained. The data set also consists of samples containing naphthenic acids having insignificant levels of alkaline-earth acid salts and samples of these same materials to which known amounts of calcium has been used to neutralize varying levels of the acids. The data set also consists of samples of materials which have naphthenic acids and contain significant levels of calcium almost entirely in the form of calcium acid-salts, such as certain crude oils. In the latter cases, the ASTM TAN levels are corrected for the presence of the calcium acid salts which are reported as TAN, and the corrected values are used in the regression model. The corrected ASTM TAN may be taken as the difference between the measured ASTM TAN and the calcium concentration, expressed in ppm, divided by 357. Thus a calcium concentration of 357 ppm as naphthenate would result in a corrected value of TAN which is 1 TAN unit less than the measured ASTM TAN.

The features of this invention include its selectivity to organic acids, its quantitation of organic acid content in ASTM TAN units, and the use of a linear multivariate model to predict acid content of a sample from its IR spectrum.

1. Acid Prediction from IR Spectra is an Application of Linear, Multi-Variate Correlation The invention makes use of a non-obvious application of multivariate modeling methods to quantify the acid content in terms of ASTM TAN. Linear, multivariate prediction methods using spectra as input are normally applied where there is no variation-in the spectral frequency position or shape of the absorption band of the molecular functionality that is relevant to the predicted parameter. If linear multivariate regression models using the spectral frequencies as independent variables are to apply, it is assumed that there is a characteristic frequency and absorption band for that functionality and, furthermore, that its contribution to the absorption spectrum of the sample changes in only in amplitude, not shape or position as a function of its concentration within the sample.

There are several reasons why the absorption frequencies of the naphthenic acids would not be considered suitable as independent variables for a linear, multi-variate regression model. First, the C=O absorption band of the acid COOH group is actually composed of C=O vibrations of a hydrogen-bonded acid dimer, and of an acid monomer, located at approximately 1709 and 1760 $cm^{-1}$, respectively. The dimer and monomer forms of the acid are in thermal equilibrium, with relative concentrations dependant upon the dissociation constant and temperature. Under measurement conditions, the spectra are strong functions of temperature, the temperature dependencies being different for different acids, for the same acid diluted in different hydrocarbon liquids, and for the same acid diluted to different levels in the same hydrocarbon liquid. Consequently, the shape and frequency position of the absorption cross-section for different acids vary depending upon the interactions with the non-acid portion of the molecule and with temperature.

As an example of the first case FIG. 7, shows the absorption cross-section in $cm^2$ per mole for several model acid compounds diluted in the same white oil matrix at a fixed temperature. It can be seen that the strength and position of the bands vary with the molecular structure.

In addition to the variation of the C=O absorption band due to intramolecular interactions, intermolecular interaction with other molecules that comprise the hydrocarbon matrix will also affect the position and shape of the bands. Thus, the Beer-Lambert law does not generally hold for organic acids. FIG. 8 curve (a) shows the absorbance per mm, absorptivity, of a single acid, cyclopentylacetic acid, diluted in a white oil to a TAN value of 3.4. Chloroform, a non-polar solvent, was added to dilute the TAN further by up to a factor of 100. The absorption band for each of the samples should differ only in amplitude and not in shape if Beer's law was valid for the acid. It is clear from curves (b)–(g) in FIG. 8 that the interaction with the solvent alters the absorption characteristics of the acid C=O.

A consequence of the non-Beer's Law behavior is the inability of a few-frequency, multi-linear regression model, to predict the acid content with sufficient accuracy for corrosion applications. This invention recognizes that the use of a multivariate principal component model transforms the measured spectral frequencies into new variables that in sufficient number can account for this non-Beer's Law behavior with sufficiently high accuracy to be of utility for corrosion applications. For similar reasons, the determination of acid reduction by peak or integrated band intensity ratios are less accurate than the approach disclosed.

For example, in the principal component regression model shown in FIGS. 2A and 2B, 10 non-sequential component variables were used, including component number 17, in order of decreasing eigenvalue, to result in a prediction error over the whole suite of petroleum crudes and pipestill and laboratory distillates, of less than 0.11 TAN units. A total of 216 samples that spanned the variability of the application was used, resulting in over 10 samples per regression component.

2. Prediction of Organic Acid Content as ASTM TAN from IR Spectra

Materials engineers and process operators have historically used ASTM TAN values to estimate the corrosivity of petroleum crude and distillate fractions. The instant invention predicts the ASTM TAN value of a sample from its IR spectrum. This was accomplished by developing a relationship between the IR spectrum and the ASTM TAN of 216 calibration samples consisting of a wide range of petroleum crude oils and distillate fractions, to enable this relationship to be used to predict the ASTM TAN of future samples.

An IR transmission cell having $CaF_2$ windows and an optical path length of 200 microns was maintained at a temperature of 65±2° C. and used to obtain the spectra of the samples. A Fourier transform IR spectrometer was used to obtain the spectra at approximately 1 $cm^{-1}$ resolution.

Only selected regions of the spectra were used to develop the calibration model. These regions are 4800–3420 $cm^{-1}$, 2770–2400 $cm^{-1}$, 2200–1550 $cm^{-1}$ and 1350–1000 $cm^{-1}$. Although the major absorbance of the acid functionality occurs in the 1800–1650 $cm^{-1}$ region, the additional spectral frequencies are critical to obtain the required accuracy and statistical measures of the quality of the model and its predictions. An example is the ability of the model to detect when a sample is a model outlier and its TAN, predicted by IR, may not be accurate.

The measured spectra in the above-mentioned spectral frequency ranges were conditioned to eliminate effects of instrumental and environmental variations which were independent of the acid content and chemical composition of the samples. The conditioning was independently applied to each frequency region.

The conditioned spectra of the calibration samples were correlated against their TAN values as determined by the ASTM D664 method. The correlation consisted of a principal component regression of spectral scores vs. ASTM D664 TAN values.

The IR TAN for the 500 calibration samples is shown in FIG. 2A. The samples have ASTM TAN values in the range 0–5. The Standard Error of Calibration was 0.09.

IR TAN predictions were carried out of 221 refinery samples including crude oils, and distillation fractions. The results are shown in FIG. 2B. The Standard Error of Prediction is 0.08.

The IR method is more repeatable than the ASTM technique. For example, using Arab light crude, the repeatability of the IR TAN is 0.008, while the ASTM method claims 0.024.

1. Selectivity to Organic Acids

The standard test method for Total Acid Number of petroleum feeds is ASTM D664-89. While the scope of this method, as stated by ASTM, is for petroleum products, it is commonly applied in the industry for crude oils and other hydrocarbon feedstocks, and for process liquids and distillation fractions, as an indicator of organic acid corrosivity. The method, however, is not selective to organic acids. Other constituents that may be present, including inorganic acids, esters, phenolic compounds, lactones, resins, salts of heavy metals, salts of ammonia and other weak bases, acid salts of polybasic acids, are titrated by the test method and reported as acid number. If present in petroleum feedstocks and process fluids, these constituents may result in ASTM TAN values which over-estimate the organic acid content. Consequently, the corrosivity may be over-estimated if a corrosion model is used to relate the TAN of the material to its corrosivity, assuming these other constituents are not corrosive.

Salts of alkaline earth metals, such as calcium, may be present in petroleum liquids as the result of natural occurrence or as reaction products of upstream treatment to neutralize part of the acid. Calcium salts of naphthenic acids are titrated and reported as acids by the ASTM method. The IR absorption due to acid carbonyl (C=O) and carboxylate anion (COO—) functionalities can be separately detected and, consequently, forms the basis for the selective prediction of organic acid content.

EXAMPLE 1

Selectivity to Organic Acids when CaO is Added to the Sample

The following example illustrates the ability of the IR to differentiate between acids and salts. A crude blend was treated to reduce the organic acid by the addition of CaO, based on ASTM TAN of the untreated crude. The addition of CaO produces soluble Ca-salts of the acids having low volatility. Upon distillation of the treated crude blend, these salts, therefore, tend to concentrate in the residuum fraction. Consequently, it may be anticipated that the ASTM method applied to this fraction will report a TAN value at levels comparable to or higher than that of the untreated crude fraction, due to the inability of the method to distinguish between acids and Ca- salts of these acids. The acid content of the residuum fraction on the other hand is, expected to be reduced from its untreated levels.

Application of the ASTM and IR TAN methods to these resid fractions result in the TAN determinations shown in Table 1. It can be seen that the ASTM TAN values are at the same level or higher as the treat increased, from B to C while the IR TAN significantly decreases with treat level as anticipated. It can be concluded that the IR gives a more reliable estimate of the organic acid TAN.

TABLE 1

| RESID FRACTION | ASTM TAN (mg KOH/g sample) | IR TAN (mg KOH/g sample) |
|---|---|---|
| A Untreated crude | 2.17 | 2.22 |
| B Treat on crude blend | 1.94 | 0.69 |
| C Treat on crude blend | 3.12 | 0.14 |

These conclusions are confirmed by the IR spectra of the untreated and treated residuum fractions. FIG. 1A shows the regions of the absorption bands of the acid C=O, aromatic C=C, and COO— carboxylate ions of the Ca salts for the distillate residuum fraction of an untreated crude oil blend (curve A), the crude oil blend treated to level B (curve b), and level C (curve c), where treat C is greater than treat B. The organic acid C=O band is reduced in curves b and c from curve a, with increasing treat. The carboxylate ion of the Ca salt on the other hand can be seen to increase in curves b and c with increasing treat. The selectivity of the IR absorbance can be more clearly displayed in FIG. 1B, where the absorbance of the untreated material is subtracted from the B and C treated materials, curves b and c, respectively, showing the loss in acid C=O and gain in the salt COO— absorption.

EXAMPLE 2

IR TAN Provides More Accurate Quantitation of Organic Acids Than ASTM TAN for High TAN Crudes Containing Organic Acid Salts of Calcium This example illustrates the application of the IR TAN invention to petroleum crude oils that contain relatively high levels of naphthenic acids and their calcium salts. This example shows that the true TAN of these crudes, as determined by the instant invention, are lower than those obtained by using the ASTM method. This is supported by showing that the calcium in the samples exist almost entirely as acid salts and account for the differences between the ASTM and IR TAN determinations.

This example also shows that the IR TAN of mixtures of these high TAN crudes blend linearly with the TAN values of the individual components weighted by their weight fraction, and that the TAN values of these blends, as determined by the IR, are lower than those obtained by ASTM. These results demonstrate that the IR TAN method can be used to blend crudes more accurately to a target TAN level for applications of the sale and purchase of crude mixtures, and for the planning of refinery processing. For example, the IR TAN method can be implemented at a pipeline or tanker terminals to control blending of the crudes to the target TAN level.

ASTM and IR TAN of high TAN crudes from three production fields, designated by B, K, and M, and zones designated by A, M, Y and 0, 1, 2, 3, have been determined and the results shown in columns 3 and 4 of Table 2, and their differences ASTM-IR, are shown in column 4. The data are presented in order of decreasing ASTM TAN.

TABLE 2

TAN and Ca Measurements on the B, M, K Crude Samples

| | TAN | | | Ca (ppm) | |
|---|---|---|---|---|---|
| SAMPLE | ASTM | IR | ASTM-IR | Acid digest. | Xylene dilut. |
| B/M2 | 7.13 | 6.71 | 0.42 | 158.0 | 160.0 |
| B/A1 | 6.25 | 5.87 | 0.38 | 43.0 | 42.7 |
| B/A2 | 6.24 | 5.92 | 0.32 | 43.0 | 42.6 |
| B/M3 | 5.88 | 5.29 | 0.59 | 78.0 | 78.1 |
| K/M1 | 5.47 | 4.13 | 1.34 | 809.0 | 803.0 |
| K/M3 | 5.38 | 3.67 | 1.71 | 834.0 | 756.0 |
| K/Y0 | 5.28 | 3.82 | 1.46 | 670.0 | 596.0 |
| K/M1 | 4.97 | 3.24 | 1.73 | 953.0 | 907.0 |
| B/M1 | 4.28 | 3.78 | 0.50 | 76.0 | 72.7 |
| K/M1 | 3.86 | 2.86 | 1.00 | 406.0 | 379.0 |
| B/M1 | 3.82 | 3.42 | 0.40 | 35.0 | 28.9 |
| K/Y0 | 1.75 | 1.47 | 0.28 | 14.0 | 14.2 |
| M/M1 | 1.30 | 1.25 | 0.05 | 2.4 | 2.7 |
| M/M1 | 0.51 | 0.39 | 0.12 | 2.5 | 1.5 |

TABLE 2-continued

TAN and Ca Measurements on the B, M, K Crude Samples

| | TAN | | | Ca (ppm) | |
|---|---|---|---|---|---|
| SAMPLE | ASTM | IR | ASTM-IR | Acid digest. | Xylene dilut. |
| K/A1 | 0.05 | 0.11 | −0.06 | 11.0 | 8.6 |
| K/A1 | 0.03 | 0.03 | 0.00 | 13.0 | 10.2 |

Also shown in the table are the results of calcium analyses using the method of Inductively Coupled Plasma (ICP) analysis. Two methods were used to introduce the samples into the plasma. One involved acid digestion of the remaining ash after combustion of the sample. The second involved dilution of the sample with xylene. The acid digestion method determines the total Ca in the sample, while the xylene dilution technique determines soluble Ca as well as insoluble Ca species having particle sizes below about 3 microns. The errors in the reported Ca values for each method are less than 5% relative.

The two measurements of the Ca level for each of the samples are given in the table. The similar values obtained by the acid digestion and xylene dilution methods are consistent with the Ca existing predominantly as soluble organic species in these samples, due to the exclusion of insoluble Ca with particle size >3 microns from the ICP in the xylene method.

FIG. 3 shows a parity plot of the ASTM and IR TAN measurements (solid circles), with error bars corresponding to the repeatability of the IR method. The parity line (solid line) is shown at the center of a band which is defined by the two dashed lines corresponding to the 6% repeatability of the ASTM TAN measurement. The IR TAN values that fall within this band agree with and are statistically equivalent to the ASTM values. Examples are the samples having the four highest and five lowest ASTM TAN-values listed in Table 1. These samples have, then, the smallest differences between the ASTM and IR TAN values.

The samples, however, whose points lie outside and to the right of the band are considered as "outliers" in the sense that they are not well predicted by the IR model when compared with the ASTM values. It can be seen from Table 1 that the largest difference between the ASTM and IR is for the K/M1 having an ASTM TAN of 5 and an IR TAN of 3.2. It will be shown, in the following, that the IR TAN values of the "outlier" samples shown in FIG. 3 are closer to the true TAN values than those obtained using the ASTM method.

The reason for the inaccuracy of the ASTM method is that the potassium, added as the potassium hydroxide (KOH) titrant, replaces part or all the calcium that is present as acid salts in the crudes. The ASTM method utilizes potentiometric detection, which, as practiced, does not distinguish the acid and salt titration end-points. Consequently, the consumption of KOH in replacement of Ca in the salts is reported as acid.

Evidence supporting the notion that the titration of organic Ca salts is the source of the difference between the ASTM and IR TAN is shown in FIG. 4. The Ca content of the samples (left ordinate axis) is plotted against the ASTM TAN. The difference (delta TAN) between the ASTM and IR TAN (right ordinate axis) is also plotted against the ASTM TAN for the corresponding samples. The coincidence of high Ca and delta TAN can be clearly seen.

It can be shown that 357 ppm of Ca is required to form the salt of 1 TAN of acid. If all of the Ca in the samples is in the form of acid salts, the ASTM method would report, for these Ca species a TAN value of Ca(ppm)/357(ppm). The reported ASTM TAN for a given sample would comprise the sum of its free acid and "Ca-equivalent" TAN contributions.

FIG. 5 shows the sum of the IR and Ca-equivalent TAN on the ordinate plotted against the ASTM TAN. The excellent agreement supports the assertion that nearly all of the Ca is present as acid salts and these salts are the source of the erroneously high values of TAN reported by the ASTM method.

Blends of the B, M, and K crudes were prepared according to the recipes given in Table 3. The ASTM and IR TAN of the blends were calculated from the measurements on the crude components and the blend recipes. Specific gravity data were required since the TAN is determined on a weight basis and the blend recipes were given on a volume fraction basis.

TABLE 3

B.M.K. Crude Blends

| | Field: | K | | | | B | | | | | M |
|---|---|---|---|---|---|---|---|---|---|---|---|
| BLEND COMPONENT | Zone: | Y0 | M1 | A1 | M3 | M1 | M2 | M3 | A1 | A2 | M1 |
| | Specific gravity | 0.941 | 0.941 | 0.941 | 0.941 | 0.934 | 0.934 | 0.934 | 0.934 | 0.934 | 0.908 |
| | ASTM TAN | 5.28 | 5.47 | 0.05 | 5.38 | 4.28 | 7.13 | 5.88 | 6.25 | 6.24 | 0.51 |
| | IR TAN | 3.82 | 4.13 | 0.11 | 3.67 | 3.78 | 6.71 | 5.29 | 5.87 | 5.92 | 0.39 |
| 1 | Volume frac. | 0.13 | 0.13 | 0.22 | 0.00 | 0.06 | 0.06 | 0.04 | 0.01 | 0.01 | 0.32 |
| | ASTM TAN (calc.) | 0.71 | 0.74 | 0.01 | 0.00 | 0.27 | 0.45 | 0.23 | 0.08 | 0.08 | 0.16 |
| | IR TAN (calc.) | 0.52 | 0.56 | 0.02 | 0.00 | 0.24 | 0.43 | 0.20 | 0.08 | 0.08 | 0.12 |
| 2 | Volume frac. | 0.16 | 0.16 | 0.21 | 0.04 | 0.05 | 0.05 | 0.02 | 0.01 | 0.01 | 0.32 |
| | ASTM TAN (calc.) | 0.83 | 0.87 | 0.01 | 0.19 | 0.19 | 0.32 | 0.14 | 0.04 | 0.04 | 0.16 |
| | IR TAN (calc.) | 0.60 | 0.66 | 0.02 | 0.13 | 0.17 | 0.31 | 0.13 | 0.04 | 0.04 | 0.12 |
| 3 | Volume frac. | 0.21 | 0.21 | 0.15 | 0.05 | 0.05 | 0.05 | 0.02 | 0.00 | 0.00 | 0.25 |
| | ASTM TAN (calc.) | 1.12 | 1.16 | 0.01 | 0.29 | 0.23 | 0.39 | 0.10 | 0.03 | 0.03 | 0.12 |
| | IR TAN (calc.) | 0.81 | 0.88 | 0.02 | 0.20 | 0.20 | 0.37 | 0.09 | 0.03 | 0.02 | 0.09 |

TABLE 3-continued

B.M.K. Crude Blends

| | Field: | | K | | | | B | | | M |
|---|---|---|---|---|---|---|---|---|---|---|
| BLEND COMPONENT | Zone: | Y0 | M1 | A1 | M3 | M1 | M2 | M3 | A1 | A2 | M1 |
| 4 | Volume frac. | 0.24 | 0.24 | 0.11 | 0.07 | 0.05 | 0.05 | 0.01 | 0.00 | 0.00 | 0.22 |
| | ASTM TAN (calc.) | 1.28 | 1.33 | 0.01 | 0.36 | 0.23 | 0.38 | 0.07 | 0.02 | 0.02 | 0.11 |
| | IR TAN (calc.) | 0.93 | 1.00 | 0.01 | 0.25 | 0.21 | 0.36 | 0.06 | 0.02 | 0.02 | 0.08 |
| 5 | Volume frac. | 0.26 | 0.26 | 0.09 | 0.09 | 0.05 | 0.05 | 0.01 | 0.01 | 0.01 | 0.18 |
| | ASTM TAN (calc.) | 1.39 | 1.44 | 0.00 | 0.47 | 0.22 | 0.37 | 0.06 | 0.03 | 0.03 | 0.09 |
| | IR TAN (calc.) | 1.00 | 1.09 | 0.01 | 0.32 | 0.19 | 0.35 | 0.06 | 0.03 | 0.03 | 0.07 |
| 6 | Volume frac. | 0.27 | 0.27 | 0.08 | 0.11 | 0.06 | 0.06 | 0.01 | 0.00 | 0.00 | 0.15 |
| | ASTM TAN (calc.) | 1.43 | 1.48 | 0.00 | 0.57 | 0.23 | 0.39 | 0.05 | 0.00 | 0.00 | 0.08 |
| | IR TAN (calc.) | 1.04 | 1.12 | 0.01 | 0.39 | 0.21 | 0.37 | 0.05 | 0.00 | 0.00 | 0.06 |
| 7 | Volume frac. | 0.27 | 0.27 | 0.10 | 0.13 | 0.06 | 0.06 | 0.01 | 0.00 | 0.00 | 0.12 |
| | ASTM TAN (calc.) | 1.43 | 1.48 | 0.00 | 0.68 | 0.24 | 0.40 | 0.04 | 0.00 | 0.00 | 0.06 |
| | IR TAN (cal) | 1.03 | 1.12 | 0.01 | 0.46 | 0.21 | 0.38 | 0.04 | 0.00 | 0.00 | 0.04 |

TABLE 4

IR and ASTM TAN on B. M. K. Crude Blends

| | ASTM TAN | | IR TAN | |
|---|---|---|---|---|
| Blend | calc. | meas. | calc. | meas. |
| 1 | 2.74 | 2.66 | 2.24 | 2.07 |
| 2 | 2.80 | 2.72 | 2.21 | 2.05 |
| 3 | 3.47 | 3.32 | 2.70 | 2.52 |
| 4 | 3.81 | 3.75 | 2.94 | 2.82 |
| 5 | 4.12 | 4.14 | 3.16 | 3.06 |
| 6 | 4.24 | 4.21 | 3.23 | 3.12 |
| 7 | 4.34 | 4.34 | 3.31 | 3.20 |

The specific gravity and volume fractions were used to obtain target weights of the components. The ASTM and IR TAN values for the components in Table 3, were calculated from the actual weights of the components used to make the blends. The calculated (from the sum of the component values in Table 3) and measured TAN for the blends are shown in Table 4 and the results displayed in FIG. 6.

Both IR and ASTM TAN blend linearly as evidenced by the small differences between the measured and calculated TAN of the blends. In addition, the true TAN values of the blends, as determined by the IR method, is significantly less than the values obtained by the ASTM method.

The true TAN values, as determined by IR, are lower than those obtained using the ASTM method on the same samples. The Ca in the crude samples appear to exist almost entirely as acid salts and account for the differences between ASTM and IR TAN measurements. Finally, studies on crude mixtures show that TAN blends linearly and the TAN values of the blends, determined by IR, are lower than those obtained by ASTM.

The conclusions show that the IR TAN method may be used to determine and report the TAN of these crudes. Commercial Fourier Transform IR hardware has been developed that is suitable for this application. Consequently, the IR TAN method can be implemented at the pipeline, tanker, or refinery to control blending of the crudes to a target TAN.

EXAMPLE 3

IR TAN Provides Accurate Quantitation of Organic Acids for Low TAN Crudes Containing Inorganic Ca-Salts A sample of low acid North Sea crude, Y, was determined to have an ASTM TAN of 1.4 and an IR TAN of 0.14, a factor of 10 lower. The ASTM value was suspect due to unusually high concentrations of Na (720 ppm) and Ca (446 ppm). If the Ca titrated is as acid, the ASTM test will result in a reported TAN of 1.25, due just to the Ca. When the calculated 1.25 Ca-equivalent TAN is added to the IR TAN value of 0.14, the calculated 1.39 result is consistent with the ASTM measured TAN of 1.4.

The crude was water-washed to remove water-soluble inorganic salts. An analysis of the washed crude confirmed the removal of nearly all of the Na (0.99 ppm) and Ca (0.59 ppm). A second IR measurement was performed on the washed crude yielding the same result (0.14) as on the original sample. A second ASTM measurement gave <0.1, consistent with the IR TAN.

The Y crude contained mostly water-soluble inorganic salts. Thus, with the removal of these inorganic salts, the ASTM TAN was significantly reduced and are comparable to the IR TAN which is unaffected by such salts.

Applications

The invention provides: the capability to accurately, precisely and rapidly determine the TAN of crudes, blends, and distillation fractions; the means to monitor and control the blending and the neutralization of organic acid species in corrosive crudes; the means of determining, monitoring, and controlling TAN in plant laboratories, on-line in refineries and at pipeline and transport terminals, and remotely for spot checks at-line, such as at storage vessels. Specifically, 1. The present invention can be used, in conjunction with corrosion models, to select and blend raw material and process unit feeds and products so that the TAN of the components and/or blend meet a target value consistent with safe and economical operations in the context of corrosion management. In a related application, the invention can also be used to monitor the TAN of process streams in order to maintain instantaneous and time-averaged TAN values within a limit as determined by plant corrosion experience. These applications are driven by the economic advantage of maximizing the usage of higher TAN feeds that are often lower-priced.

An example of this feed blending application is shown in FIG. 9. Feed Tank 1 (FT1) contains single high TAN crude, or a blend of two or more high TAN crudes. Feed Tank 2 (FT2) contains a single low-to-medium TAN crude, or a blend of two or more such crudes. These Feed Tanks are connected to a mixing valve (MV) whose output TAN (TANB) is determined at a measuring point (MP) by the on-line IR TAN analyzer (A) embodying the present invention. TANB is supplied to a control system (CS) along with a desired target TAN (TANT) determined by a target model (TM) based on corrosion experience and safety and reliability constraints. A signal from the control system is fed back to the mixing valve to vary the amounts of material from both feed tanks until the target TAN is obtained (i.e., when TANT-TANB=0), thereby minimizing feed costs.

2. The invention can be used by supply personnel, planners, and assay database managers to valuate candidate raw materials (e.g. crudes) and make purchasing and pricing decisions based on the corrosivity of such materials as inferred by their TAN. When embodied in a transportable analyzer configuration, the invention can provide on-the-spot evaluations of raw material TAN prior to the commitment to purchase of large quantities.

FIG. 10 shows an example where a crude sample (S) is collected from a storage or shipboard tank (T) and the IR spectrum obtained by a portable FT-IR TAN analyzer (A). The TAN value, along with other valuation parameters such as yield, sulfur and metals content, and gravity, is provided as input to a mathematical model (M) that calculates a range of values, in dollars per barrel, for example, for the crude price.

As an alternative to collecting a sample a portable analyzer can be used with an optical probe (P), which can be inserted into the crude. The spectrum is obtained via an optical fiber (F) linking the analyzer to the probe. The probe heats the sampled portion of crude so as to obtain the spectrum at the same temperature as that of the calibration samples used to build the IR TAN model.

3. This invention can be used to monitor the crude TAN from different wells within a given field or from several fields and blend these crudes to a target TAN for transport and sale. The monitoring and blending can be carried out on-line or at-line at pipelines, tankers, or blending stations. It has been shown earlier that the crude TAN blends in proportion to the TAN values weight fraction of its components.

FIG. 11 shows the means for on-line blending of crudes produced from 3 different wells (W1, W2, and W3) directly into a pipeline (PL). A portion of the output from W1, W2, and W3 is switched, on demand from the analyzer (A), by valves V1, V2, V3, respectively, to a filter (F) which removes water and solids that melt above the sample measurement temperature. The filtered crude flows into the FT-IR analyzer (A), which heats the sample, and determines its TAN (TAN1, TAN2, and TAN3) from its IR spectrum. The main output from W1, W2, and W3 flows into a mixing valve system (MVS), that includes means to determine the specific gravity and volumetric flow rate of each of the flows, and that controls the weight fraction of each to produce the blend (B), which enters the pipeline (PL). A portion of the blend is switched, on demand from the analyzer (A), by valve (VB), to the filter (F) and the analyzer (A) that determines its blend TAN (TANB). The blend and target TAN values (TANB and TANT) are transmitted to the control system (CS) that controls the mixing valve system (MVS), according to a control algorithm that includes well depletion and other production factors and economics, to adjust the flows of W1, W2, and W3 to make the difference between the blend and target TAN zero.

4. The invention can be used to monitor and control TAN reduction processes, such as neutralization of the corrosive organic species. For example, a method to optimize a neutralization process is shown in FIG. 12. In this embodiment the invention serves as both a feed-forward and feed-back controller to optimize the neutralization process. The hydrocarbon feed in this example may be, but is not limited to, a whole or topped crude, and the neutralizing agent may be, but is not limited to, an oxide, hydroxide, or hydrate of calcium.

The target levels of organic acids for petroleum feeds and processed fractions are currently measured by a potassium hydroxide titration, such as ASTM D664, and reported as Total Acid Number (TAN). Corrosion rates in process equipment are estimated from these TAN values using corrosion model. Instantaneous or averaged TAN limits for the feed and processed fractions are generally established corresponding to critical corrosion rates.

TAN values obtained by such methods are unreliable when the hydrocarbon contains oxides, hydroxides, hydrates, and salts of certain metals, such as calcium. These species may be native to the crude or may be present in neutralizing agents. Consequently, existing methods cannot be used to reliably optimize neutralizing processes without first separating these species or their reaction products from the hydrocarbon. The model-based IR method described below is the preferred optical absorbance method to be used in this invention. It is selective to acids, insensitive to acid type and interactions with other constituents in the untreated or treated feed, can be implemented on-line, and is sufficiently rapid to enable process control and optimization.

The invention may be described with reference to FIG. 12. In this embodiment the invention serves as both a feed-forward and a feed-back controller to optimize the neutralization process. The hydrocarbon feed in this example may be, but is not limited to, a whole or topped crude, and the neutralizing agent may be, but is not limited to, an oxide, hydroxide, or hydrate of calcium.

An infrared spectrum of the feed is measure at point A prior to its entering the mixing valve through which water (desalter water) is typically added for desalting. The spectrum signal is input to the IR TAN and/or corrosion rate model from which a TAN value and/or corrosion rate, respectively, for the feed is predicted. The TAN/corrosion rate value is compared with the relevant feed TAN and/or corrosion rate control limit values in the analyzer and a feed rate of neutralizing agent is estimated by the analyzer. The process controller sets the neutralizing agent control valve to provide this initial feed of neutralizing agent to the mixing valve. The feed/neutralizing agent/desalter water mixture is introduced into the desalter. The temperature, pressure, and residence time of the mixture in the desalter are such as to both effectively reduce the salt and water content of the mixture and to neutralize the acid to the targeted value of TAN and/or corrosion rate.

An IR spectrum of the treated feed is obtained, at point B, upon its emergence from the desalter. The spectrum signal is used with the relevant prediction model to estimate the TAN and/or corrosion rate of the treated feed. The difference between the predicted and target values of the TAN and/or corrosion rate value is used by the process controller to correct the setting of the neutralizing agent control valve so as to achieve the target value. The entire feed-forward and feed-back process control sequence can be repeated to provide, on-line optimization of the neutralization process.

If the control limit (sidestream TAN and/or corrosion rate control limit) is determined based upon the TAN and/or corrosion rate caused by a sidestream or fraction of a processing unit, such as single or multiple stage pipestill rather than feed TAN and/or corrosion rate, infrared spectrum needs to be acquired of the limiting sidstream shown as point C, for example. Alternatively, and more preferably the sidestream TAN and/or corrosion rate can be predicted from a measurement of the untreated and treated feed. By obvious extension, other or additional points in the processing equipment, such as the furnace outlet can similarly be monitored and provide relevant control limits.

The invention claimed is:

1. A method to determine the organic acid content of petroleum streams comprising:
   (a) irradiating a sample of said petroleum stream with IR radiation;
   (b) determining an IR absorbance spectrum wherein said IR radiation is only in the spectral ranges having wavelengths 1000–1350 $cm^{-1}$, 1550–2200 $cm^{-1}$, 2400–2770 $cm^{-1}$ and 3420–4800 $cm^{-1}$; and
   (c) correlating all of said wavelengths of said IR absorbance spectrum determined in step (b) with the organic acid content of said petroleum stream using linear multivariant regression analysis.

2. The method of claim 1 wherein said organic acid content is in units of ASTM Total Acid Number TAN.

3. The method of claim 1 further comprising the step of heating a sample of said petroleum stream having boiling points below 1050° F., at a temperature between 25° C. and 125° C. during said irradiating step.

4. The method of claim 3 wherein said temperature is between 40° C. and 100° C.

5. The method of claim 4 wherein said temperature is between 55° C. and 75° C.

6. The method of claim 1 wherein the IR absorbance for every spectral frequency is between 0 and 2.0 absorbance units.

7. The method of claim 5 wherein the IR absorbance for every spectral frequency is between 0 and 1.75 absorbance units.

8. The method of claim 3 wherein said sample is a mixture of petroleum streams having a boiling point below 1050° F.

9. The method of claim 4 wherein said sample is a mixture of petroleum streams having a boiling point below 1050° F.

10. The method of claim 1 wherein said IR radiation is in the spectral ranges 1000 and 4800 $cm^{-1}$.

11. The method of claim 1 further comprising the step of orthogonalizing the IR absorbance spectrum so as to eliminate environmental and instrumental contributions.

12. The method of claim 1 further comprising the step of using said IR absorbance spectrum of a set of samples, the calibration samples, which are representative of the variability of petroleum feed and process streams, to develop a prediction regression model having regression factors to predict the TAN of said streams to predetermined accuracy.

13. The method of claim 12 wherein said number of samples is at least 8 times the number of regression factors in the model.

14. The method of claim 12 wherein said samples include both whole crudes and pipestill distillation factions.

15. The method of claim 12 wherein average prediction error for a sample set of whole crude and pipestill and laboratory distillation fractions are less than 0.25.

16. The method of claim 1 utilizing a sufficient number of calibration samples to achieve a predetermined accuracy.

17. The method of claim 16 wherein said number of calibration samples exceed 100.

18. The method of claim 16 wherein said number of calibration samples exceed 400.

19. A method to optimize blending of two or more petroleum feedstreams including organic acids having different levels of Total Acid Number TAN wherein the feedstream blend is processed into process streams comprising:
   (a) blending said feedstreams predetermined proportions to form a feedstream blend;
   (b) measuring the TAN level of said feedstream blend and/or said processed streams using the method of claim 1;
   (c) comparing the TAN level of said feedstream blend and/or process streams to a predetermined TAN level; and
   (d) adjusting the proportions of said feedstreams in the blending step so that the TAN level of the feedstream blend and/or process streams is equal to or less than said predetermined level.

20. In a method for determining the TAN value of a crude oil including organic acid, the improvement which comprises determining the TAN level of the crude oil by the method of claim 1.

21. A method to optimize the addition of organic acid neutralizing agents to a petroleum feedstream that is processed into process streams comprising:
   (a) determining the IR absorbance spectrum of the feedstream and/or processed streams wherein said IR radiation is only in the spectral ranges having wavelengths 1000–$1350^{-1}$, 1550–2200 $cm^{-1}$, 2400–2770 $cm^{-1}$, and 3420–4800 $cm^{-1}$; and
   (b) predicting the organic acid content and/or corrosion of the feedstream and/or processed streams from all of said wavelengths of said IR spectrum determined in step (a);
   (c) adding the neutralizing agent in batch or intermittent or continuously mixed flow;
   (d) measuring the IR spectrum of the treated feedstream and/or processed streams;
   (e) predicting the remaining acid content and/or the corrosion rate of the treated feedstream and/or processed streams without removing the neutralized products or unreacted neutralizing agent; and
   (f) controlling the amount or blend of neutralizing agents, and/or the temperature, pressure, mixing, or flow conditions in the neutralizing process to achieve the target acid level and/or corrosion rate in the treated feedstream and/or processed streams.

22. The method of claim 1 wherein said sample is a mixture of petroleum streams having a boiling point above 1050° F.

23. The method of claim 12 wherein said number of samples is at least 10 times the number of regression factors in the model.

24. The method of claim 12 wherein said average prediction error for a sample set of whole crude and pipestill and laboratory distillation fractions are less than 0.15 TAN units.

* * * * *